_United States Patent_ [19]

Rothberg et al.

[11] Patent Number: 5,422,690
[45] Date of Patent: Jun. 6, 1995

[54] FITNESS IMPAIRMENT TESTER

[75] Inventors: Michael Rothberg, Foothill Ranch; Tom N. Cornsweet, Irvine, both of Calif.; Marc D. Rafal, Montgomery County, Md.

[73] Assignee: Pulse Medical Instruments, Inc., Rockville, Md.

[21] Appl. No.: 191,590

[22] Filed: Mar. 16, 1994

[51] Int. Cl.$^6$ .............................................. A61B 3/14
[52] U.S. Cl. ................................. 351/209; 351/221; 128/745
[58] Field of Search ............... 351/205, 209, 210, 221, 351/200; 128/745

[56] References Cited

U.S. PATENT DOCUMENTS

| | | | |
|---|---|---|---|
| 4,850,691 | 7/1989 | Gardner et al. | 351/221 |
| 4,854,329 | 8/1989 | Walruff | 128/745 |
| 5,196,872 | 3/1993 | Beesmer | 351/208 |

FOREIGN PATENT DOCUMENTS

2185815  7/1987  United Kingdom ............... 351/209

_Primary Examiner_—William L. Sikes
_Assistant Examiner_—Huy Mai
_Attorney, Agent, or Firm_—Whtiham, Curtis, Whitham & McGinn

[57] ABSTRACT

A fitness impairment tester implements a self-administered screening test to determine whether a subject is physically impaired. The tester is fully automated to respond to the entering of a subject's personal identification on a keypad. By superposing two different colored lights as viewed through an eyepiece, the subject aligns his or her pupil on the optical axis of pupil imaging optics which focuses an image of the subject's pupil on an image plane. The tester automatically recognizes this condition and audibly signals the subject that the test is about to begin. Light stimuli are provided to cause the pupil to change size and the eye to move. Pupil diameter measurements are made of the image of the subject's pupil in response to on axis light stimuli. Eye tracking of the subject's eye in response to moving light stimuli provide a measure of eye movements. The data acquired by measuring pupil diameter and saccadic movements of the subject's eye as a function of time are compared with baseline data for the subject stored in a database, and an output indicative of a deviation of said current measurements from said baseline data is provided.

17 Claims, 9 Drawing Sheets

FITNESS IMPAIRMENT TESTER

BACKGROUND OF THE INVENTION

Field of the Invention

The present invention generally relates to apparatus for testing for impairment in the physical performance of individuals, and especially those individuals who may be engaged in the operation of potentially dangerous equipment. More particularly, the invention is directed to an apparatus which is sensitive to changes in the state of a person's central nervous system, whether due to illness, fatigue or the influence of alcohol and drugs.

Description of the Prior Art

Government statistics demonstrate that certain risk factors are associated with traffic accidents. For example, the proportion of fatally injured drivers testing positive for alcohol is markedly higher for those drivers at fault than for those not at fault. Other drugs, such as marijuana, cocaine, opiates and amphetamines are similarly cited as increasing the risk of accidents. Similarly, illness and fatigue can adversely affect the performance of an individual in the operation of a vehicle, whether a private automobile or a commercial conveyance such as a bus, train or airplane. Obviously, the risk factor is magnified many times in the case of commercial transportation due to the number of passengers involved. Moreover, the problem of physical impairment is not limited to the field of transportation, as it has been recognized that there are many other fields, such as the operation of machine tools and heavy equipment, where such impairment places the operator of the tools or equipment at great personal risk.

The general problem is well recognized and has led, in certain cases, to strict laws and regulation, both on the state and federal levels, to prohibit operation of certain types of equipment by individuals who are physically impaired due, for example, to alcohol or drugs. However, such laws and regulations do not address those cases where an individual is not physically impaired due to alcohol or drugs, but may be ill or fatigued. Moreover, laws and regulations usually are invoked only after the fact of an accident.

In an effort to address the problem prospectively, millions of dollars are spent each year in both the public and private sectors to educate the public concerning the potential risks of operating equipment while physically impaired. Unfortunately, recent research casts doubt on the ability of individuals to recognize and to make accurate judgements about the amount of their own impairment. For example, it is generally well recognized that many persons consistently underestimate the level of impairment after consuming even a small quantity of alcohol. It is probable that this is generally true no matter what the source of the physical impairment.

What is needed, therefore, especially for high risk activities, is a way to provide an objective determination of a level of physical impairment of individuals who are about to engage in high risk activities. The problem is that the risk associated with factors such as alcohol, drugs and fatigue are not always easily demonstrated by individual performance on highly learned tasks such as those used in performance testing. Overt performance deficits, such as decreases in eye-hand coordination, cognitive skills or short term memory are not reliable indicators, for an individual, of the presence of these risk factors except at the extremes. Even when overt performance deficits are not present, covert performance deficits can significantly impact safety. Covert performance deficits exists when the measured performance levels of highly learned tasks are normal but the ability to recognize and react to new or unexpected situations is impaired.

SUMMARY OF THE INVENTION

It is therefore an object of the present invention to provide an objective way to screen for the presence of risk factors associated with both overt and covert performance deficits.

It is another object of the invention to provide a self-administered test which reliably and accurately identifies those workers who are at increased risk to themselves, their co-workers and the public.

It is a further object of the invention to provide a device which performs a completely safe, non-invasive test that causes the subject no discomfort and provides an immediate result as to the physical impairment of the subject.

According to the invention, there is provided a device which performs a brief eye test to screen for the presence of risk factors. A completely automated and self administered test uses involuntary eye responses that are sensitive to such risk factors as alcohol, drugs and fatigue. By testing involuntary responses, the device is not influenced by learning or motivation. A complete test takes approximately thirty seconds.

Baselines are a key part of the operation of the device. According to one aspect of the invention, a baseline is established for each individual by taking repeated tests during an initial time period. This baseline contains all the information necessary to compare a current reading to the expected range of responses for that individual. A test result indicates whether the current measure, compared to that of the individual's baseline, is within an expected range of day-to-day variation. If the difference is larger than this expected range, the individual fails the test. Alternatively, baselines can be based on a large population. In this case, the baseline is used in the same way but is less sensitive than individual baselines.

To stimulate the pupil response, the device provides controlled flashes of light with retinal intensity that is constant regardless of pupil size. To stimulate eye movements, light targets are made to move along a precise path. Under computer control, the device measures pupil diameter sixty times each second and eye position nine hundred times each second. Infra-red light, illuminating only the inside of the eye, is scattered by the retina and reflected back out of the pupil. This light forms an image on an infra-red sensitive video sensor, such as a charge-coupled device (CCD). Tracking of eye movements keeps the image at the center of the camera. The device provides extremely accurate measurements of pupil diameter, constriction amplitude and saccadic eye movement velocity. The device also provides very accurate and repeatable measures of pupil latency, which is an important additional predictor of central nervous system integrity.

In one preferred embodiment of the invention, the device was implemented as a portable device, approximately the size of a catalog case, allowing the device to be set up on a table top. In this implementation, the device can be used for gathering the baseline response data for individuals. In another preferred embodiment of the invention, the device may be mounted in a wall adjacent an entry way. When so mounted, an eye piece and a numerical keypad are provided so that the subject may enter a personal identification number and then look into the eyepiece for a brief test, the result of which would be a simple pass or fail. The subject may be informed of test completion by an audible signal or other appropriate means. The test result may be evidenced by a printout and accumulated in the subject's data file.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The invention tests involuntary reactions of the eye to controlled stimuli. Movements of the eyes and pupils are sensitive to factors that effect the central nervous system. Because the neural pathways that carry visual information from the eyes and the control information back to the eye muscles cover a significant portion of the brain, a change in brain function is likely to alter the control of one or more of the eye functions. This basic relationship is well recognized in the medical arts, and a routine physical examination typically includes observing eye movement and the reaction of the pupils to light as a coarse assessment of neurological integrity. The subject invention provides three fundamental capabilities that dramatically improve on this technique. First, the invention makes highly accurate and repeatable measures of pupil size, eye position and their dynamic changes. Second, the external stimulus conditions that force these changes are precisely controlled. Third, the invention compares these measurements with a previously established baseline for each subject. If the results of this comparison are within a statistically determined range, the result is reported as a PASS. If the comparison is outside that range, the result is reported as a FAIL. No judgment as to the underlying cause may be made. Rather, the tested subject should receive additional attention to determine what conditions might be present.

Figure 1:
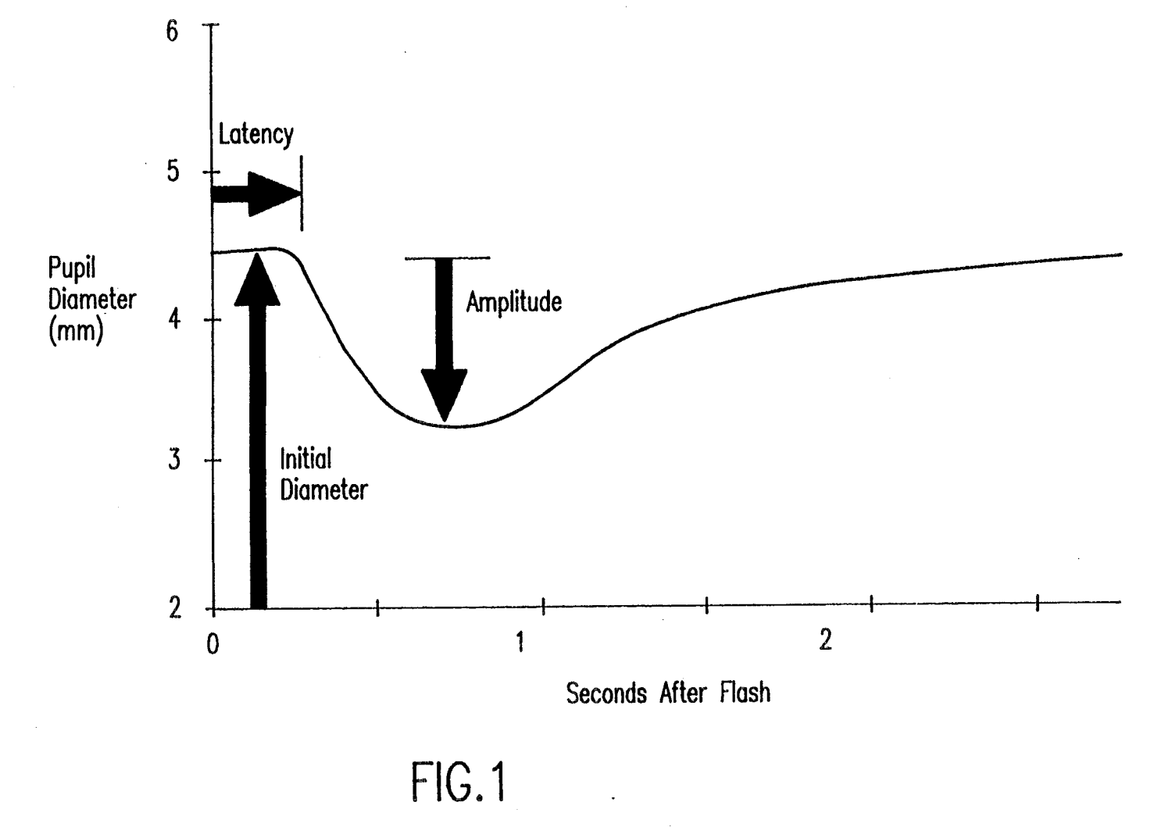
FIG. 1 is a graph showing a typical pupil response to a 0.1 second light flash used in a preferred embodiment of the invention.

Referring now to the drawings, and more particularly to FIG. 1, there is shown a graph of a typical pupil response to a 0.1 second light flash used in a preferred embodiment of the invention. The flash is initiated at "0" seconds. Before the flash occurs and for a period of about 250 milliseconds after its onset, the pupil has a relatively constant diameter which is labeled "Initial Diameter". This diameter is one of the parameters evaluated by the invention. The period between the onset of the flash and the beginning of the response is called the "Latency" and is the second parameter evaluated. The pupil then responds by constricting briefly and finally returns to its initial diameter. The extent of this constriction is labeled "Amplitude" and is a third parameter evaluated. As will be explained in more detail hereinafter, a fourth parameter evaluated is that of "Saccadic Velocity", which is the average velocity of rotation of the eye, measured in degrees per second, as the subject responds to an abrupt change in target position. This parameter is measured by tracking the eye movement that results from precisely controlled moving light stimuli.

While the preferred embodiment of the invention measures Initial Diameter, Latency, Amplitude and Saccadic Velocity in order to evaluate fitness impairment, other parameters could be measured, either in addition to or instead of some of the parameters measured. Examples of other such parameters are maximum constriction velocity, time constant of the constriction, redilation time constant, and the like. In particular, our tests have shown that redilation speed is an important measure of fatigue. Table 1 summarizes the impact of various factors on the eye as described in the literature.

TABLE 1

| Factor | Major Effect on the Eye Noted |
| --- | --- |
| Marijuana | Reduced Constriction Amplitude |
| Cocaine | Increased Diameter |
| Heroin, Codeine and other Opiates | Reduced Diameter, Reduced Saccadic Velocity |
| Amphetamines | Increased Diameter |
| Alcohol | Decreased Saccadic Velocity |
| PCP | Reduced Constriction Amplitude |
| Fatigue | Decreased Diameter and Unstable Responses |
| Central Nervous System Disorders | Varies by Location of Damage |
| Retinal Damage | Reduced Constriction Amplitude |

In a preferred embodiment of the invention, each individual baseline consists of eight numbers computed from several repeated test results taken for that individual. From that sample of tests, a mean, and a standard deviation, a, are computed for each of the three pupil parameters shown in FIG. 1 and for Saccadic Velocity. A typical baseline is shown in Table 2.

TABLE 2

| Parameter | Description | Baseline Values | |
|---|---|---|---|
| Diameter | Initial pupil diameter just prior to light flash. | $\mu_{INI}=$ 4.6 mm | $\sigma_{INI}=$ .21 mm |
| Amplitude | Difference between initial pupil size and minimum pupil size. | $\mu_{AMP}=$ 1.1 mm | $\sigma_{AMP}=$ .09 mm |
| Latency | Time from start of flash to start of constriction. | $\mu_{LAT}=$ 260 msec | $\sigma_{LAT}=$ 10 msec |
| Saccadic Velocity | Average velocity of rotation of eye in response to 28° change in target position. | $\mu_{SV}=$ 349°/sec | $\sigma_{SV}=$ 17°/sec |

While the preferred embodiment of the invention uses eight numbers in the baseline data, this number may be increased to ten or more. For example, a mean, $\mu$, and a standard deviation, a, of redilation velocity, a parameter affected by fatigue, could be added to the eight numbers used in the baseline data of Table 2.

Using the individual baseline, the invention computes an Index that measures the similarity of a current response to the baseline, as follows:

$$\text{Index} = \sum_{i=1}^{n} \left( \frac{P_i - \mu_i}{\sigma_i} \right)^2, \tag{1}$$

where $P_i$ is a parameter, $\mu_i$ is the mean for the parameter, and $\sigma_i$ is the standard deviation for the parameter, there being n parameters. For example, a preferred embodiment of invention computes the Index as $$\text{Index} = \left( \frac{INI - \mu_{INI}}{\sigma_{INI}} \right)^2 + \left( \frac{AMP - \mu_{AMP}}{\sigma_{AMP}} \right)^2 + \left( \frac{LAT - \mu_{LAT}}{\sigma_{LAT}} \right)^2 + \left( \frac{SV - \mu_{SV}}{\sigma_{SV}} \right)^2, \tag{2}$$

where INI is the Initial Diameter, AMP is the Amplitude, LAT is the Latency, and SV is the Saccadic Velocity of the current measured response.

Large values of Index indicate that the current parameter values are very different than those of the baseline. The characteristics of the chi-square distribution are used to determine the value of Index below which a desired proportion of normal tests will fall. The relative likelihood that a particular value of Index will occur is given by the probability density function. p(Index), of the chi-square distribution with four degrees of freedom:

$$p(\text{Index}) = \frac{\text{Index}}{4} \cdot e^{-\frac{\text{Index}}{2}}. \tag{3}$$

Figure 2:
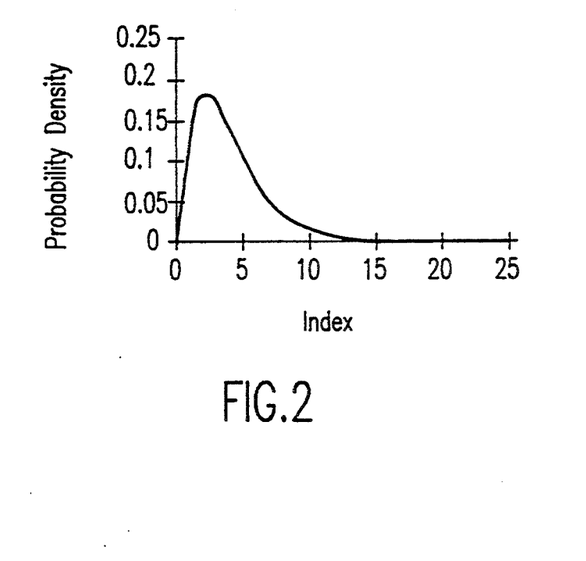
FIG. 2 is a graph showing the probability density function for Index.
Figure 3:
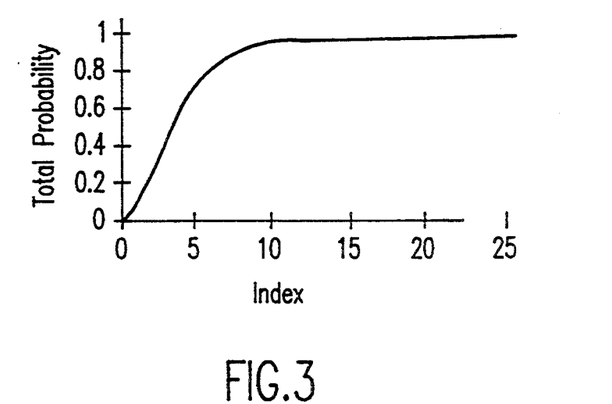
FIG. 3 is a graph showing the total probability for Index.

The total probability, P(Index), that a given result will fall below a specific value of Index is found by integrating the probability density, p(Index), between the limits of 0 and that value: FIG. 2 shows the relative likelihood that the given value of Index will occur. For example, an Index value near two is the most likely value $$P(\text{Index}) = \int_0^{\text{Index}} p(x)dx = 1 - \left( \frac{\text{Index}}{2} + 1 \right) \cdot e^{-\frac{\text{Index}}{2}}. \tag{4}$$

while an Index value of near ten occurs one tenth as often. While FIG. 2 shows the probabilities associated with a specific value, FIG. 3 shows the overall likelihood that a result will fall anywhere below a value. For example, 99.9% of test results of normal subjects will fall below an Index value of 18.467. This value can then be used as a threshold with which to judge test results. If Index is greater than the threshold, the preferred embodiment of the invention reports the result as FAIL.

It should be understood that there are other statistical formulae that could be used to make a pass/fail judgement. Each formula answers a different statistical question. This formula implemented answers the question, what is the probability that the current values of the parameter set could occur for this individual under the same condition as obtained during collection of baseline data conditions? If that probability is sufficiently small (say 0.1%), the result is a fail and it is assumed that something is not normal. Other statistical questions are possible. For example, a regression analysis might answer the question, is it more likely that the current set of parameters would occur for this individual under normal conditions or under the influence of marijuana? Such a regression analysis could be done for each risk factor for which data is available. In the preferred embodiment of the invention, a result reported as FAIL makes no declaration of the underlying cause; however, it should be understood that it is possible to make clear statements in many cases because different classes of drugs affect the measured parameters differently, as does fatigue.

With reference again to FIG. 1, when repeated samples are obtained for a given individual, the values of Initial Diameter, Latency, Amplitude, and Saccadic Velocity will be very similar under normal conditions. There are, however, a number of factors that can profoundly change an individual's response. The invention provides extremely accurate measurements of pupil diameter and constriction amplitude and very accurate and repeatable measures of latency. We have found that latency is an important predictor of central nervous system integrity. In addition, the invention provides extremely accurate measures of saccadic velocity. Validation of the operation of the invention has been carried out in controlled scientific studies at major research institutions.

A complete test using the invention takes approximately thirty seconds and is self administered. A printed test receipt, available immediately, can provide a record of the result of the test. For workers in jobs classified as safety sensitive, employers can use the invention at the beginning of each shift. Each worker takes the thirty second test as part of the routine check-in procedure and provides their supervisor with the printed test receipt before the worker is allowed to begin the shift.

Figure 4:
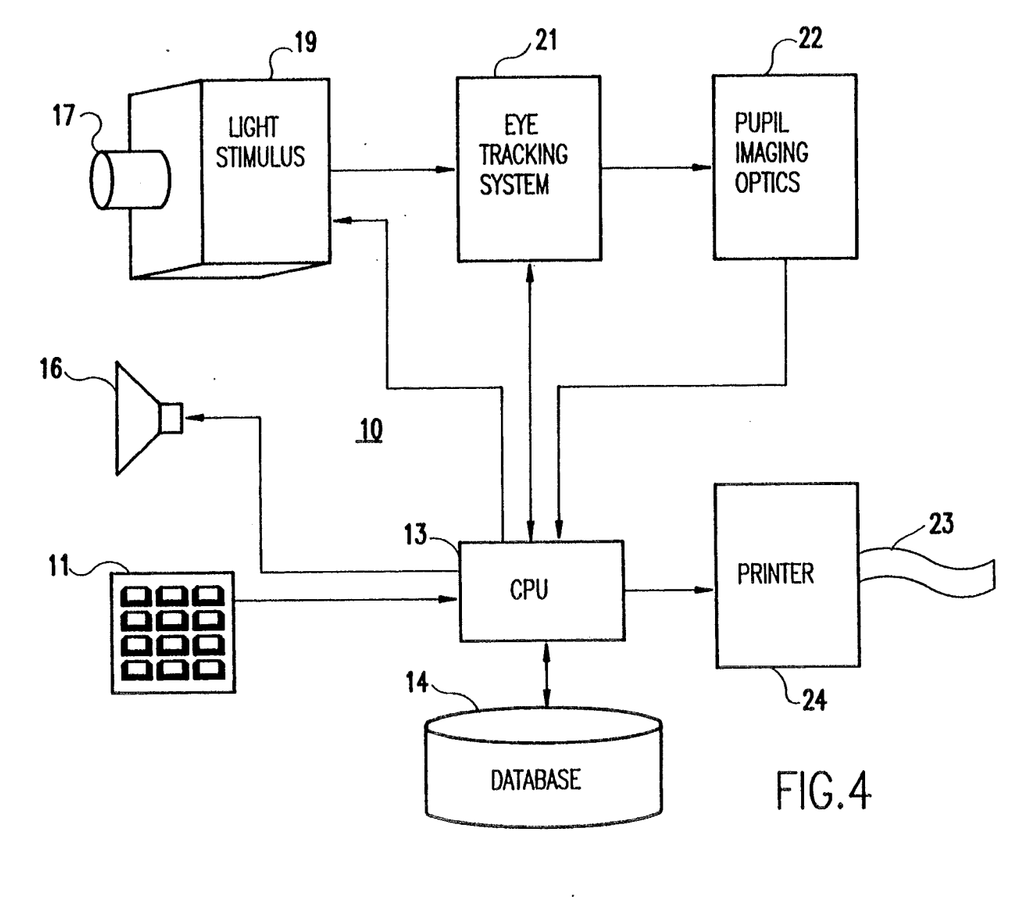
FIG. 4 is a block diagram showing the the functional components of a preferred embodiment of the invention.

FIG. 4 shows the block diagram of the functional components of a preferred embodiment of the invention. The device 10 includes a keypad 11 for input of a subject's identification number. This information is processed by the computer 13 and used to access the subject's baseline data from database 14. Once the computer 13 has determined the subject's PIN to be valid, an audible signal is provided by speaker 16 indicating that the device is ready to begin a test.

Baselines are a key part of the operation of the invention. During baseline data collection, the instrument is controlled by an operator who instructs the subject, enters the subject's identification number and other personal information, and runs the test. The baseline is established for each individual by taking repeated tests, and calculating the mean and standard deviation from the group of tests, storing in a baseline table in database 14 which is later accessed during routine testing. This baseline contains all the information necessary to compare a current reading to the average response.

During routine testing (i.e., after baseline data have been collected and results stored in the database 14), the following procedure is followed. Initially, the instrument is in a standby mode, in which nothing is operating except those aspects of the system that are required to sense entries on the keypad 11. First, the subject enters his or her identification number on the keypad 11. The entered identification number is checked by the instrument to determine whether it is valid; that is, whether or not it matches an identification number in the database 14. If not, an error tone is sounded on speaker 16. If the number is valid, the instrument is ready for a test. The test begins when the subject places their eye up to the eyepiece 17 and the instrument recognizes their pupil to be in the correct position. Upon completion of a test, the instrument compares the values of a set of parameters derived from the measurements with a corresponding set derived from the baseline data in database 14 and computes the results of the test, printing either a PASS or FAIL receipt 23 on printer 24 or printing FAULT, if the test did not terminate successfully. Following printing, the instrument returns to a standby mode.

Figure 5:
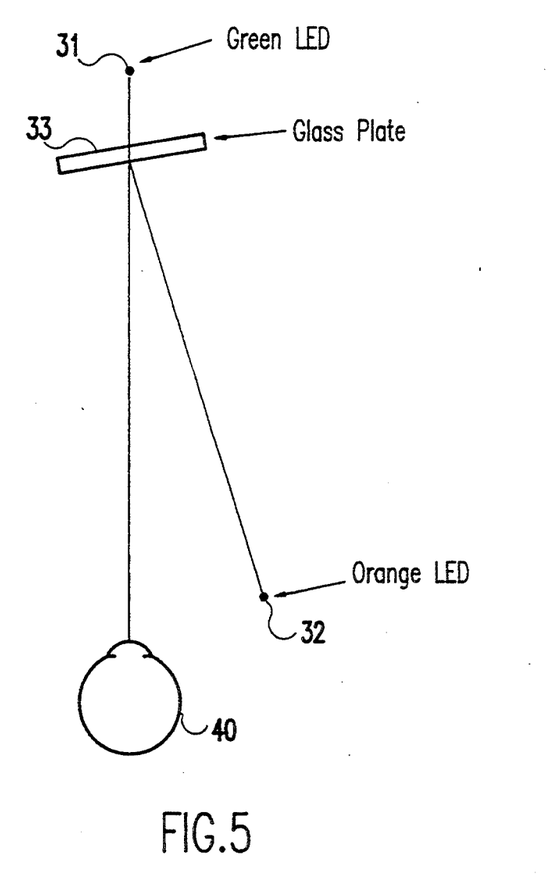
FIG. 5 is a schematic diagram showing the optical location of green and orange lights used to align the eye to an optical axis.

When notified that the device 10 is ready to begin a test, the subject looks into the eyepiece 17. The first thing the instrument must do is to decide whether or not a pupil is present in approximately the right position; that is, aligned with the optical axis of the instrument. The subject assists in obtaining optical alignment by looking through the eyepiece 17 while the eye is a few inches away from the instrument. At that point, the subject sees a small orange and a small green light. FIG. 5 shows the optical locations of a green light emitting diode (LED) 31 and an orange LED 32. The green LED 31 is viewed directly through the pane of glass 33, while the orange LED 32 is viewed by reflection from the glass 33. The optical distance from the eye 40 to the orange LED 32 is about twice the optical distance from the eye to the green LED 31. Therefore, when the subject moves their head horizontally or vertically, a motion parallax is produced causing one light to move with respect to the other. The goal is to give the subject information allowing him or her to place the eye on the optical axis of the measuring optics. This is accomplished by the subject moving sideways and up or down until the orange and green lights appear to be superimposed. At this point, the subject then moves up to rest against a rubber eyecup 18 while maintaining the superposition of the two lights.

Figures 6, 6A:
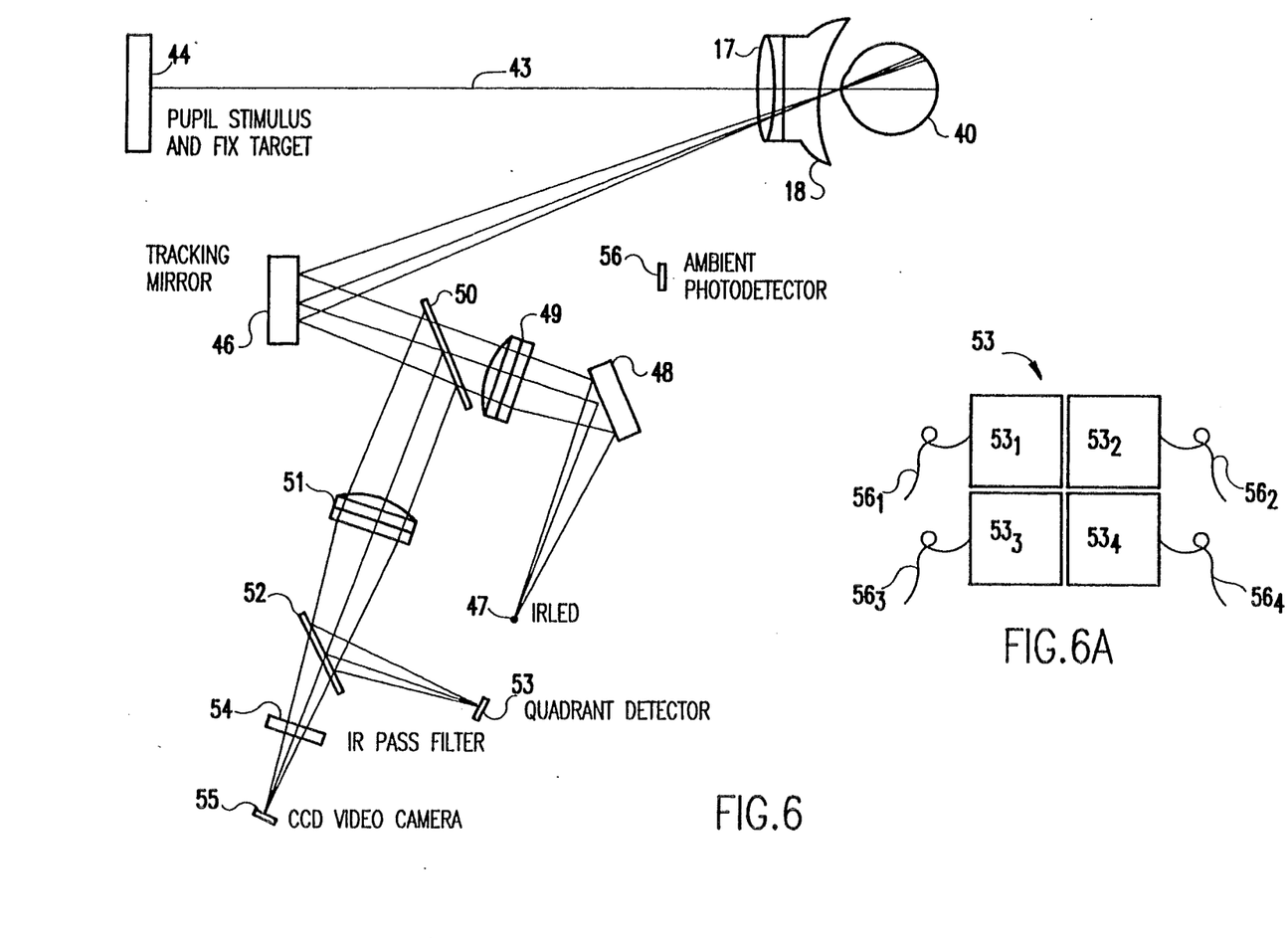
FIG. 6 is a schematic diagram showing the optical components of the eye tracking and pupil imaging systems.
FIG. 6A shows a detail of the quadrant detector.

In FIG. 4, the computer (or microprocessor) 13 controls an eye tracking system 21 in a feedback loop. The eye tracking system 21 provides an output to pupil imaging optics 22 which, in turn, provides an output to the computer 13. FIG. 6 shows in schematic form the basic components of the eye tracking system 21 according to a preferred embodiment of the invention. The subject's eye 40 is positioned relative to the eyepiece 17 having a eyecup 18 so that initially the subject's gaze is aligned along center line 43 toward a pupil stimulus and fixation target 44.

The tracking system itself includes a tracking mirror 46 which pivots about two perpendicular axes. The pupil of the subject's eye is illuminated by an infrared (IR) light emitting diode (LED) 47. The light from the LED 47 is reflected by a fixed mirror 48 through an imaging lens 49 and beam splitter 50 to tracking mirror 46. The IR light is reflected by the tracking mirror 46 through the eyepiece 17 to the subject's eye 40, where it forms an image of IR LED 47 that is much smaller than the smallests that the pupil ever gets. The light thus passes through the pupil and falls on the retina, where it is backscattered.

Backscattered light that exits the eye through the pupil is reflected by the mirror 46 to beam splitter 50 which reflects the light through imaging lens 51 and an IR pass filter 54 to a second beam splitter 52. Part of the IR light is reflected by the beam splitter 52 to a quadrant detector 53, shown in more detail in FIG. 6A, and part of the IR light is passed by the beam splitter 52 to a video camera 55, typically in the form of a charge coupled device (CCD). The beam splitter 52, IR filter 54 and CCD sensor 55 constitute the pupil imaging optics 22 shown in FIG. 4.

In an application of a preferred embodiment of the invention, the camera 55 is used for making pupil diameter measurements during a part of a test procedure. The tracking system is independent of the camera and pupil diameter measuring system and, therefore, that system will not be described in detail here. For a description of a suitable system for measuring pupil diameter, see U.S. Pat. No. 5,196,872 to Beesmer et al. The camera video can also be used to correct certain kinds of errors, particularly those associated with the use of stepper motors as positioning motors for the tracking mirror. For example, when the eye moves slowly and smoothly (i.e., "pursuit movement"), the motor position of course consists of a series of steps, which, if plotted, make it look like the eye is stepping instead of moving smoothly. However, for these slow movements, the video rate is fast enough that motion of the image across the camera can be measured between motor steps. The tracking mirror tries to null the movements of the image of the eye, but the tracking mirror being driven by a stepper motor, moves in steps; however, if the eye is moving smoothly, its image will move smoothly between steps. Thus, by measuring the displacement of the video and adding it to the motor position display, a better representation of what the eye is actually doing is achieved.

The tracking system uses a quadrant detector 53, instead of the camera 55. A plan view of the quadrant detector 53 is shown in FIG. 6A and comprises IR detectors $53_1$, $53_2$, $53_3$, and $53_4$, one for each of first, second, third, and fourth quadrants of an image plane onto which an image of the subject's pupil is projected by the beam splitter 52. Wires $56_1$, $56_2$, $56_3$, and $56_4$, respectively connected to IR detectors $53_1$, $53_2$, $53_3$, and $53_4$, carry analog signals corresponding to the amount of IR light falling on the corresponding detector. These analog signals are combined and digitized for processing by the computer 13.

If the pupil is approximately aligned, light from the IR LED 47 enters the pupil about at its center and illuminates the retina. Light backscattered from the retina that emerges from the pupil is split by beam splitter 50 and again by beam splitter 52. Half of the light passing through beam splitter 50 forms an image of the pupil on a CCD sensor 55 and the other half forms an image of the pupil approximately centered on the silicon quadrant photodetector 53. To begin testing, a decision regarding whether or not a pupil is present and being properly imaged must be made by the computer 13. That decision is based upon the intensity and the distribution of light falling on the CCD sensor 55. If the eye is entirely absent and nothing lies in front of the eyepiece 17, and negligible light is reflected to the CCD sensor 55, the instrument will not initiate testing. If light does not fall on the CCD sensor 55 in this case, it will also fall on the ambient light photodetector 56 and the computer 13 will initiate testing.

This decision process is implemented as follows. A value of the video level, called THRESHOLD_LOW. is chosen to be just greater than the video level in the absence of any object in front of the eyepiece 17 that would reflect light back to the CCD sensor 55. The "pupil diameter" determined using that threshold, called DIAMETER1, will be zero if no reflecting surface is present. One of the criteria for PUPIL_PRESENT is that DIAMETER1 exceeds a user-settable threshold called MINIMUM_DIAMETER. If an eye is in front of the eyepiece 17 and properly centered then the small spot of IR light emerging from the instrument will enter the pupil, scatter from the retina, and backlight the pupil. If the eye is approximately at the correct distance from the instrument, the bright pupil image will be sharply focussed on the CCD sensor 55. However, if the eye is not centered, the light emerging from the instrument will illuminate some part of the eye other than the pupil, e.g., the eye lid. In that case, light reflected back into the instrument will produce a bright spot on the CCD sensor 55, but it will not have sharp edges. Similarly, if the light enters the pupil but the eye is far enough away from the instrument that the pupil image is badly defocused, it will not have sharp edges. Therefore, the second set of criteria for PUPIL_PRESENT are related to the sharpness of the image on the CCD sensor 55. These criteria can be understood by referring to FIGS. 7, 8 and 9.

Figure 7:
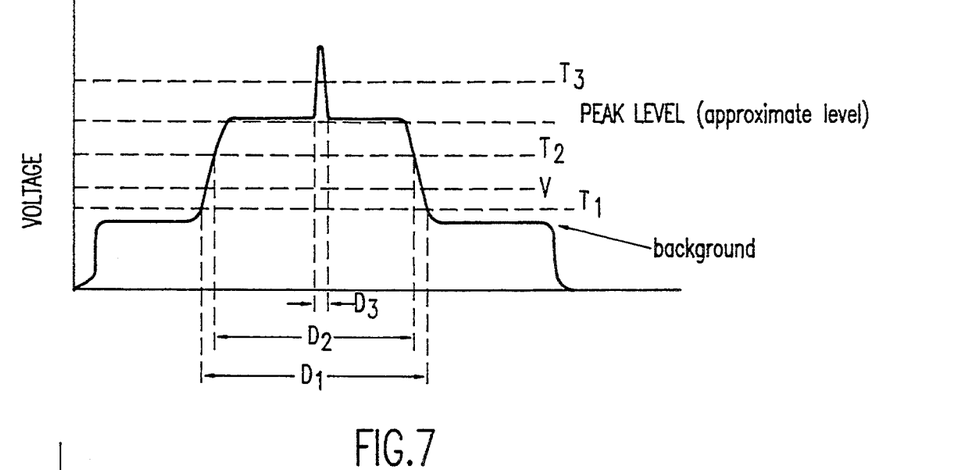
FIG. 7 is a plot of the video signal on one horizontal line through the middle of a typical sharp image of the pupil on a sensor.

FIG. 7 is a plot of the video signal on one horizontal line through the middle of a typical sharp image of the pupil on CCD sensor 55. The horizontal axis represents either time or distance and the vertical axis, either image brightness or video voltage. The lowest level, labeled "background", is the level due to stray light and miscellaneous sources of noise. The wide pedestal with sloping sides in the middle is the pupil image, and the narrow spike at the center is a reflection from the cornea. The geometry of the optics is such that the corneal reflection is minimized and often absent.

Figure 8:
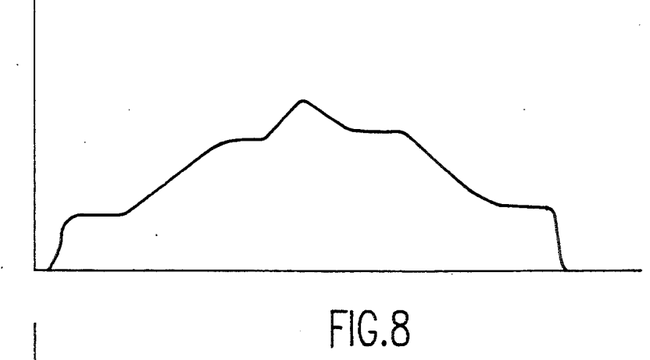
FIG. 8 is a plot of the video signal if the pupil is on axis but too far from the instrument causing the image to become defocused.
Figure 9:
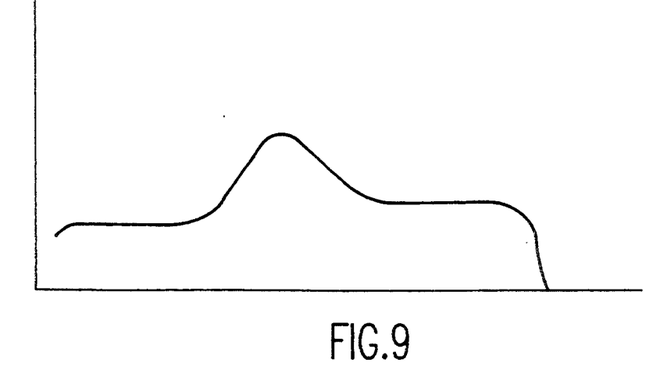
FIG. 9 is a plot of the video signal if the light does not fall on the pupil but instead on the sclera or eye lid.

If the pupil is on axis but too far from the instrument, the image becomes defocused, as in FIG. 8, and if the light does not fall on the pupil but instead on the sclera or eye lid, the image is as in FIG. 9. Only FIG. 7 represents the state that is called PUPIL_PRESENT. To make this determination, three threshold levels are set, indicated as T, $T_2$ and $T_3$ in the figures.

$T_1$ is a constant set to be slightly above the background level. $T_2$ is dynamically set in the following way. At the end of each horizontal line, the electronic hardware sends a value to the computer 13 that represents the peak of the low-pass filtered video signal level. This level is called PEAK_LEVEL, and because of the filtering, it typically falls at about the level indicated in FIGS. 7, 8 and 9. $T_2$ is set to be a fixed distance (called T_DELTA_NEG) below PEAK_LEVEL, that is, $$T_2 = PEAK\_LEVEL - T\_DELTA\_NEG,$$

where T_DELTA_NEG > 0. However, for reasons that are explained below, it is important that $T_2$ not be too close to $T_1$, as it might become if PEAK_LEVEL drops too low. Therefore, if $T_2$, as determined above, falls below a particular value, V, it is reset to equal V, where V is significantly above $T_1$, as indicated in FIG. 7.

The third threshold, $T_3$, is set to a fixed distance, called T_DELTA_POS, above PEAK_LEVEL, that is, $$T_3 = PEAK\_LEVEL + T\_DELTA\_POS,$$

where T_DELTA_POS > 0.

For each threshold level, a diameter can be determined; e.g., $D_1$, $D_2$ and $D_3$, respectively. If there is nothing in front of the eyepiece 17, the $D_1$ will be zero. The first criterion for PUPIL_PRESENT is that $D_1$ exceeds a small criterion value called MINIMUM_DIAMETER. If the image is sharp as in FIG. 7, the diameters $D_1$ and $D_2$ will be close to equal. Therefore, a second criterion for PUPIL_PRESENT is that $D_1-D_2$ must be smaller than a criterion value, called V1_2.

Sometimes an image that is not a pupil image will have steep enough slopes that the above criterion is satisfied as, for example, if the light level in FIG. 9 were substantially increased. To handle that contingency, a third criterion is imposed, namely that the difference between $D_2$ and $D_3$ must be greater than a criterion amount, called V2_3.

In summary, PUPIL_PRESENT is true if $$\begin{cases} D_1 \geq MINIMUM\_DIAMETER, \text{ and} \\ (D_2 + V1\_2) \geq D_1, \text{ and} \\ (D_3 + V2\_3) < D_2 \end{cases}$$

Occasionally, the instrument is positioned so that, with no subject in place, light from a lamp or window enters the eyepiece and illuminates the CCD sensor 55 in a way that satisfies all the above conditions. To prevent this from causing the instrument to begin testing, a second photosensor 56, shown in FIG. 6, within the instrument but well away from the optical axis, is monitored. If room light enters the instrument, it will illuminate this detector, but when the eye is in place, the detector is not illuminated. The instrument will not initiate a test unless the signal from this second photosensor 56 is below a threshold level.

If the eye is sufficiently well centered and approximately in focus, the computer 13 causes the instrument to automatically initiate the testing sequence, as explained below, and sounds a beep on speaker 16 to signal the subject that this is so. If no beep sounds, the subject moves a little side to side or up and down until the beep does sound. The test then proceeds automatically until it is complete, at which point another beep is sounded on speaker 16 and all the lights in the instrument are turned off.

Returning to FIG. 4, the computer 13 controls the light stimulus component 19 during the test. This component, shown in more detail in FIG. 10, provides a light stimulus to the subject in the form of light flashes, causing the pupil to contract, and lights at different locations within a hemisphere of view, causing the subject to rotate his or her eye to gaze at the location of the light.

Figure 10:
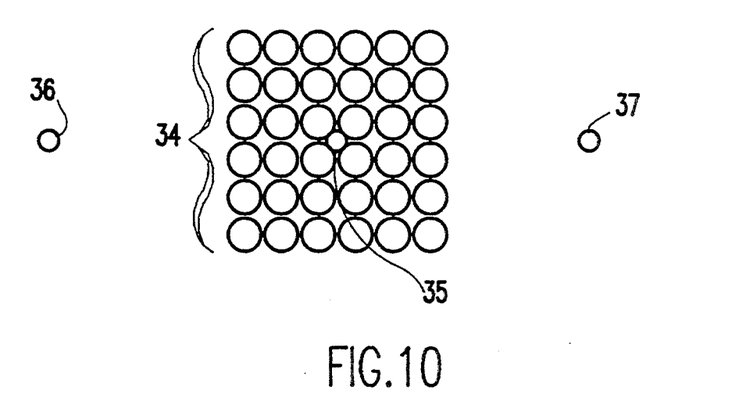
FIG. 10 is a pictorial diagram showing the configuration of the light stimulus component of the preferred embodiment of the invention.

With reference to FIG. 10, there is shown an array of large circles 34 which represent the pupil stimulus LED array. This array produces bright flashes of light used to stimulate pupil responses which are measured by the subject invention. Within the LED array is a smaller circle 35 which represents the fixation point; that is, this is the optical location of the superposition of the light from the green and orange LEDs 31 and 32 shown in FIG. 5. The outer two smaller circles 36 and 37 are LEDs used to stimulate saccadic movements. These LEDs are abruptly turned on an off in a controlled sequence to stimulate the subject to rapidly rotate his or her eye.

Referring again to FIG. 4, pupil imaging optics 22 provide an input to the computer 13 which the computer uses to calculate pupil diameter and pupillary response. The preferred technique for calculating pupil diameter is disclosed in U.S. Pat. No. 5,196,872 issued to Ross J. Beesmer et al. and assigned to the assignee of this application. As described in that patent, the pupil diameter is determined by counting clock pulses during which the video level from each horizontal line scan of the CCD sensor 55 exceeds a threshold. At the end of each video field, the longest of those lengths is reported to the computer 13 and is taken as the "diameter".

When the instrument first comes out of its standby mode, and before PUPIL PRESENT is determined, the camera gain and the intensity of the IR LED 47, shown in FIG. 6, that illuminates the pupil are not always optimal for subsequent tracking and eye measurement. Therefore, immediately upon PUPIL_PRESENT being satisfied, these two levels are set as follows.

Recall that an image of the pupil is formed on the quadrant detector 53 (shown in more detail in FIG. 6A). Three output channels convey information from this detector to the computer 13, a "horizontal difference" voltage, indicating the difference in amounts of light falling on the left versus the right halves of the detector, a "vertical difference", and a "sum" (of all four quadrants), indicating the total amount of light falling on the entire detector. The current through the IR LED 47, and therefore its intensity, is automatically adjusted so that the "sum" equals a criterion level, which is near but below the saturation level of the quadrant detector. If the reflectance of the subject's retina is so low that the "sum" cannot reach the criterion, the current is set at the maximum possible level. Then, the gain of the camera is automatically adjusted so the PEAK_LEVEL equals a criterion value. This gain level yields an image that is well above the noise level but does not saturate the camera.

Once the levels have been set, tracking is enabled. Eye tracker 21 provides another input to the computer 13 which the computer uses to calculate saccadic velocity during eye pursuit. The basic tracking algorithm is as follows. If the horizontal error signal indicates that the pupil image is horizontally displaced from the center of the quadrant detector by an amount greater than a threshold amount, the stepper motor (not shown) that causes the tracking mirror 46 to move about a vertical axis is driven by computer 13 in a direction that reduces the horizontal error signal. Similarly, the vertical error signal is reduced by controlling the stepper motor (again, not shown) that causes the tracking mirror 46 to move about a horizontal axis. If, during tracking, PUPIL PRESENT should turn false and stay false for two seconds, e.g., the subject moves away from the instrument or tracking has failed, then tracking is disabled and an error message is presented via printer 23.

It is useful for a number of reasons, one of which is related to blink detection, to detect the occurrence of rapid eye movements, i.e., saccades. SACCADE goes true when a tracking motor has stepped in the same direction on more than a criterion number of successive motor clock cycles; that is, when a stepper motor has been going as fast as it can for more than a criterion number of steps. SACCADE remains true until a clock cycle occurs during which the motor does not step in the same direction.

When a blink begins, the light distribution on the quadrant detector 53 can cause the apparent position of the pupil to change rapidly, which in turn can cause the tracking mirror 46 to move to a new position such that when the eye opens again, the optical axis will miss the pupil and tracking will be lost. It is therefore important to detect a blink as early in is course as possible, so that tracking can be disabled and then re-enabled at the end of the blink. Whenever a variable called BLINK is true, tracking is suspended and the tracking mirror 46 is held at the position it held immediately before BLINK went true.

Figure 11A:
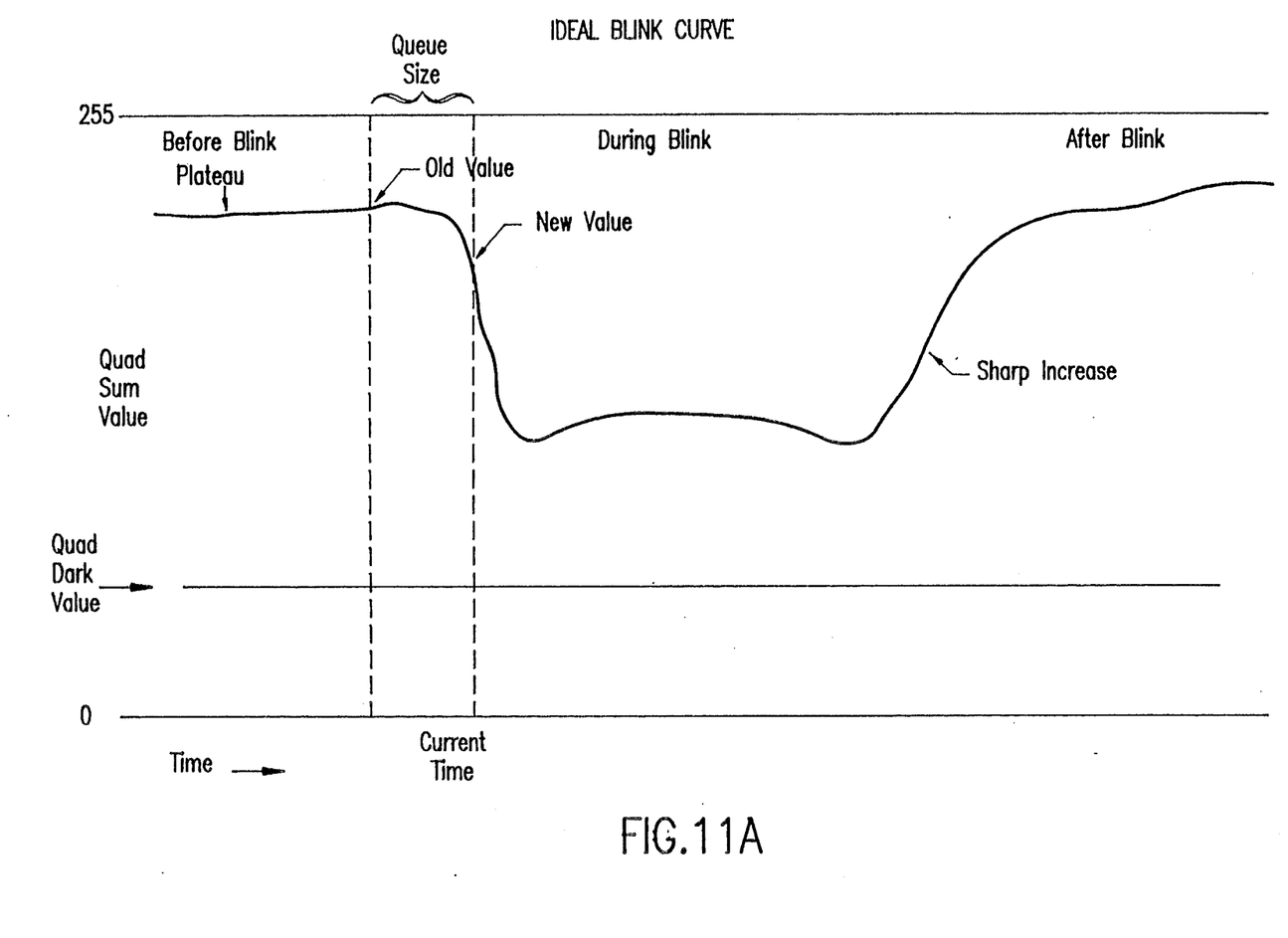
FIG. 11A is a graph showing an ideal blink curve.
Figure 11B:
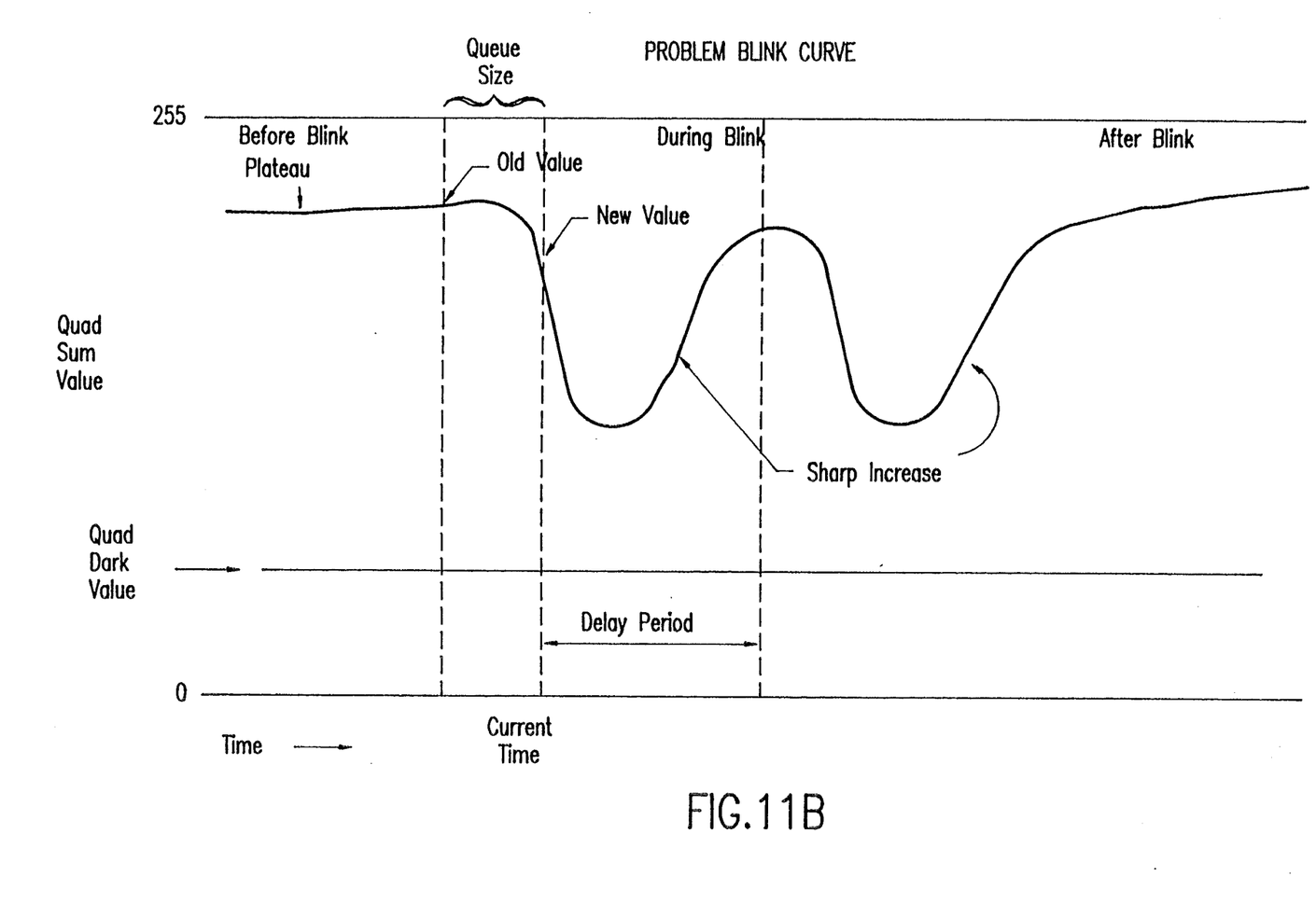
FIG. 11B is a graph showing a problem blink curve used to illustrate the process of recognizing a blink.

When the servo is tracking properly, the backlit image of the pupil will remain entirely on the quadrant detector 53, and the total amount of the light on the quadrant detector will be equal to the product of the area of the pupil by the flux density of the pupil light. These two values will vary over time depending on the subject's angle of gaze and pupil diameter; hence, the quadrant detector sum value will vary over time. However, the rate of change in the quadrant detector sum from these two factors is small compared to the rate of change in the quadrant detector sum value that occurs when the subject blinks. More particularly, as the eyelid cuts across the backlit pupil, several factors combine to cause a rapid change in the quadrant detector sum, as typified by the quadrant detector sum curve in FIG. 11A. Even in the case where the amount of light falling on the quadrant detector is very close to the amount when the eye is open, as in the case of very small pupils, there is always a rapid change in the sum signal as the eyelid closes and opens, as shown in FIG. 11B.

Since the plateau level of the sum signal (defined as the signal level when the eye is open) will vary with gaze angle and pupil diameter, setting up a fixed threshold value, above which the eye is open and below which the eye is closed, to detect blinks cannot work. So in order to detect a blink, the blink detector subsystem must detect the rapid decrease in signal directly and, as soon as possible, stop the servo loop subsystem, then look for the rapid increase in sum value that occurs at the end of a blink and restore the servo loop subsystem to normal operation. It should be understood that it is important to disable the servo loop system as early in the blink as possible. When the light reflected from the eyelid falls on the quadrant detector 53 replacing the light from the pupil, the resulting signal from the quadrant detector has no relationship to the pupil position and may result in a very large servo error signal. Such a large servo error signal can have the effect of causing the servo loop subsystem to move the tracking mirror away from its current (and correct) location as quickly as possible. On the other hand, when the eyelid has opened, the erroneous quadrant detector difference signal is replaced by a valid pupil signal that will generally have a small servo error.

The challenge in detecting these rapid changes in signal lies in the need for speed. Any algorithm to perform this function will be invoked at each interrupt. i.e., 900 times a second, prohibiting the use of normal floating-point techniques for finding the slope of a curve; e.g., regression line. What is needed is a highly efficient technique that is insensitive to high frequency noise, as a two-point slope calculation would be. Basically, this is done by storing the incoming quadrant detector sum values in a first-in. first-out (FIFO) type queue of length N and comparing the oldest and newest values. If the difference between these two values is greater than, say, 20% of the active signal, then a rapid decrease in signal is occurring, signifying the start of a blink.

The newest value in the queue that was just read from the quadrant detector is called "New_Value" and the oldest value in the queue is called "Old_Value". The "Dark_Value", which was determined prior to enabling the servos, is an indicator of the noise level on the quadrant detector. "Delay_Count" is the number of clock ticks that must pass after the "Subject Is Blinking" condition goes true before the conditional "Sharp_Increase" can be set true. The value of "Delay_Count", which is fixed at compile time, is determined so that the delay time is long enough to get beyond the first sharp increase on the Problem Blink Curve shown in FIG. 11B.

The following code is executed after each servo interrupt:

```
if Subject_Is_Blinking then
if Delay > 0 then
Delay ← Delay - 1;
if (New > Old + Delta*2) and (Delay = 0) then
Sharp_Increase ← true
if (New_Value > Blink_Stop_Level) and Sharp_Increase then
Subject_Is_Blinking ← false
else "Do if subject is not blinking"
Sharp_Increase ← false
Delay ← Delay_Count
Active_Signal ← Old_Value - Dark_Value
Delta ← Active_signal / 10 "Integer division"
Blink_Start_Level ← Old_Value - Delta*4
Blink_Stop_Level ← Old_Value - Delta*2
if New_Value < Blink_Start_Level then
Subject_Is_Blinking ← true
```

Figure 12:
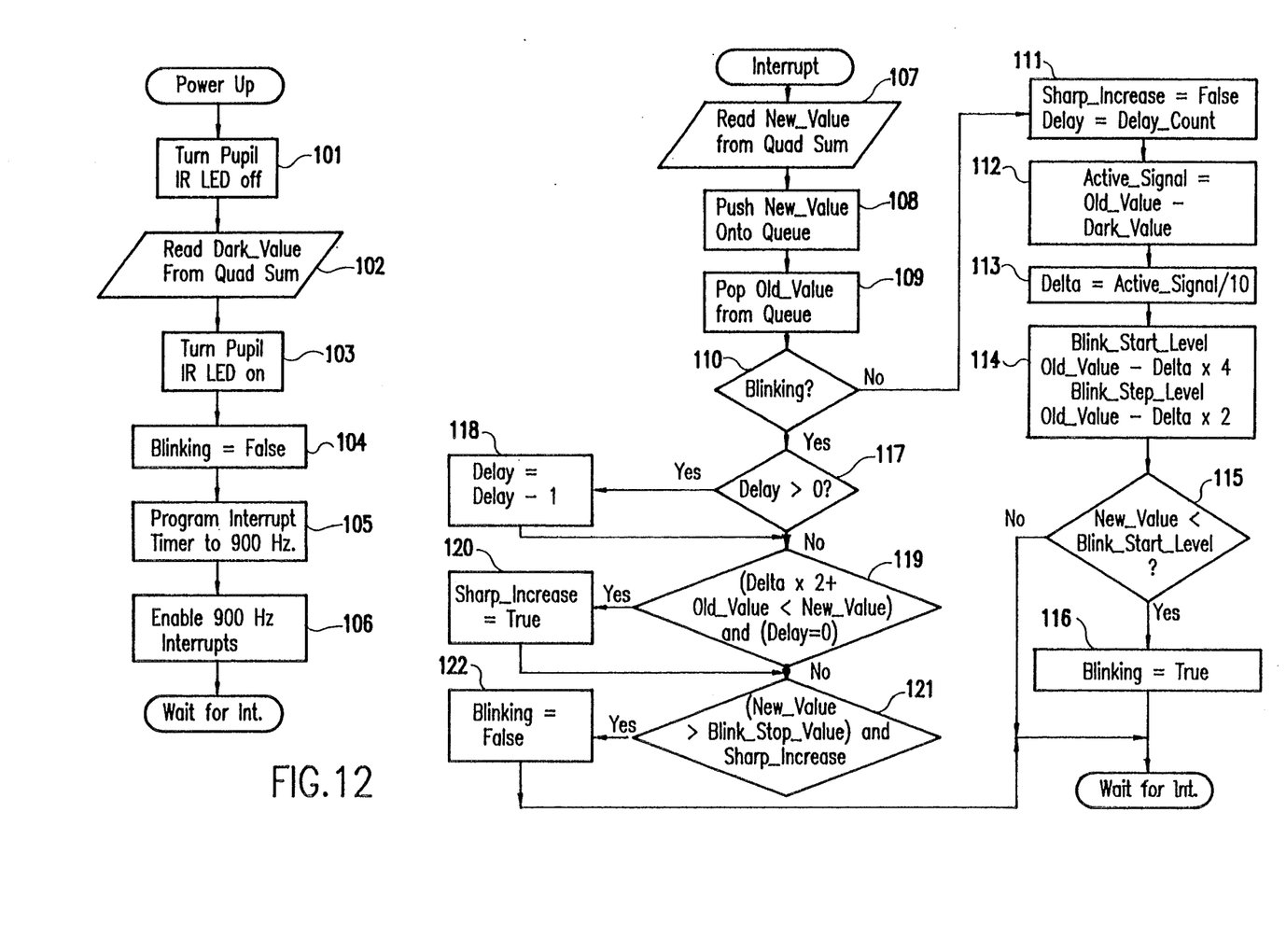
FIG. 12 is a flow diagram showing the logic of the software subsystem that controls the microprocessor of the system to perform blink detection.

FIG. 12 is a flow diagram showing the logic of the blink detector subsystem which implements the pseudocode above. At power up, the pupil IR LED 17 is held in the off condition in function block 101, and the Dark_Value is read from the quad detector 53 output in operation block 102. The IR LED 47 is then turned on in function block 103, and blinking is set to false in function block 104. The program interrupt timer is set to 900 Hz in function block 105, and the 900 Hz interrupts are enabled in function block 106. The subsystem at this point is initialized and waits for an interrupt. When an interrupt is received, the New_Value is read from the quad sensor sum output in operation block 107. The New_Value is pushed into the queue in function block 108, and the Old_Value is popped out of the queue in function block 109. A test is made in decision block 110 to determine if blinking is detected. If not, Sharp_Increase is set to false and the delay is set to Delay_Count in function block 111. Next, in function block 112 the Active Signal is set to Old_Value less the Dark_Value measured on initialization. Delta is set to Active Signal divided by ten in function block 113, and in function block 114, Blink_Start_Level is set to Old_Value minus four times Delta and Blink_Step_Level is set to Old_Value minus two times Delta. A test is then made in decision block 115, to determine if New_Value is less than Blink_Start_Level. If so, Blinking is set to true in function block 116 and the subsystem waits for the next interrupt; otherwise, the subsystem simply waits for the next interrupt.

Returning to decision block 110, if Blinking is detected, a further test is made in decision block 117 to determine if the value Delay is greater than zero. If so, the value Delay is decremented by one in function block 118; otherwise, no change is made to the Delay value. A test is then made in decision block 119 to determine if two times Delta plus Old_Value is less than New_Value and Delay is equal to zero. If so, Sharp_Increase is set to true in function block 120: otherwise, no change is made. Then, in decision block 121, a test is made to determine if New_Value is greater than Blink_Stop_Value and Sharp_Increase is true. If so, Blinking is set to false in function block 122 and the subsystem waits for the next interrupt; otherwise, the subsystem simply waits for the next interrupt.

One last point about the "Subject_Is_Blinking" flag. When this condition becomes true, motor movement must be suspended as soon as possible; however, if a motor is traveling at a speed greater than the stop-start speed of that motor and the step commands to the motor are immediately aborted, the motor will still continue to move under mechanical inertia, resulting in the microprocessor losing track of the motor's position. The way around this problem (and an example of the subtle interaction between these three software subsystems) is not to suspend the servo loop during a blink but to set the servo error to zero instead. This achieves the suspension of motor activity but without the possible loss of step integrity that may result without the graceful ramping down of the motors as needed.

It will be appreciated from the foregoing that the eye tracking system according to the invention provides a significant advance in the art of tracking fast eye movements. By illuminating the retina of the eye with a spot of light that is small enough in the pupil plane that it never hits the iris, the light scattered back from the retina and out of the pupil results in an image on the four quadrant detector that looks like a bright disk on a dark background, which is the optimum to furnish error signals to a position measuring system. Although optimum, the signals are not linear. Since the pupil is round, the change in voltage difference between, say, the left and right halves of the quadrant detector is not linear with the amount of decentering of the pupil and, in fact, depends on the size of the pupil. However, what is important is that when the signals are equal from all four quadrants, by definition the pupil image is centered on the quadrant detector, and any departures from equality signal that the pupil is not centered on the detector.

In the practice of the invention, both the input light and the light emerging from the pupil are reflected from the tracking mirror 46. The electronics and tracking program are designed so that if the signals from the quadrant detector indicate that the pupil image is decentered, say, to the left, then the mirror will rotate, moving the pupil image toward the right. Therefore, the tracking system keeps the pupil image centered on the quadrant detector. If the eye moves, decentering the pupil, the system moves the tracking mirror just enough to compensate.

The tracking mirror 46 does something else that is quite important. The input light enters the eye in a very small spot that does not hit the iris. Were the light to hit the iris, the image on the quadrant detector would be an image of the spot hitting the iris so that when the eye moved, the iris moving under the spot would result in the spot not moving with respect to the optical system, so its image would not move on the quadrant detector. In other words, an eye movement would not be signaled unless the light enters the pupil and misses the iris. Then if the eye moves, the pupil moves, so the input light has to move too, in order to stay centered. That happens in the eye tracking system according the invention because the input light is also reflected from the tracking mirror. Thus, the tracking mirror 46 compensates for eye movements to keep the pupil image centered on the quadrant detector 53 and at the same time the input light centered on the pupil.

By backlighting the pupil while avoiding illumination of the iris, a simple image of far more contrast than any other system known is achieved, but in order to do so in the presence of any significant movement, the pupil must be accurately tracked. In order to track saccadic movements, the tracking has to have a high sampling rate (or be an analog system with a high frequency response). In the preferred embodiment using stepper motors, the quadrant detector amplifiers have cutoff frequencies well above 1 kHz and their outputs are sampled and the stepper motors that drive the tracking mirror are stepped, 900 times per second. It would also be possible to use the analog outputs of the horizontal and vertical quadrant amplifiers to drive, directly, analog linear actuators, e.g., voice coils, which in turn drive the tracking mirror.

In order for the tracking servo subsystem to work optimally, two special control subsystems have been added. These are the pupil recognition and blink detection subsystems. If there is no blink detection, then when the eye blinks, the system will usually lose tracking because the input illumination will then fall on the eyelid, leaving the tracking servo system in an open loop condition. That is, the tracking mirror can move without causing any change in the error signal. This is because the mirror moves both the input and output paths. If the mirror moves, the spot falling on the eyelid will move, but that movement will be exactly compensated for by the mirror, keeping the image stationary on the quadrant detector. Thus, the blink detector subsystem locks the tracking servo subsystem in place until the blink is over, on the assumption that the eye will not move so far during the blink that when the eye opens, the spot will miss the pupil. This assumption is true for most cases. The pupil recognition subsystem is needed so that, if the system loses tracking with the result that the light spot does not enter the pupil, loss of tracking can be recognized. Similarly, when a test is started automatically, that is, without needing an operator, the system has to know that a pupil is there before tacking is activated and the test started.

While the eyelid is closed during a blink, tracking will be suspended for the reasons given above. If tracking were to be enabled the instant that BLINK went false during reopening after a blink, the tracking mirror could be driven to a false position on large pupils, and tracking would be lost. Therefore, tracking is not reenabled until a preset period of time after BLINK goes false.

During very rapid (saccadic) eye movement, the video image will sometimes satisfy both of the blink criteria described above even though no blink is actually occurring. Obviously, if BLINK went true and tracking were suspended during an eye movement, tracking would be lost. To avoid this possibility, a third condition is included in the blink detection algorithm, namely that while SACCADE is true, BLINK cannot be true.

Based on measurements performed during a test, the computer 13 computes the values of Diameter, Amplitude, Latency, and Saccadic Velocity from the subject's responses to the light stimuli. Using these values and accessing the $\mu$s and $\sigma$s of the subject's individual baseline values from database 14, the value Index is computed using Equation (1). The value Index is then compared to a predetermined threshold by the computer 13, and the result is reported by printing a receipt 23 using printer 24. The result is also stored with a date and timestamp in the database 14 for archival purposes and later access. If the value of Index is above the predetermined threshold, the result is reported as FAIL.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A fitness impairment tester comprising:
   pupil imaging optics and focusing an image of the subject's pupil on an image plane;
   pupil diameter measurement means for measuring diameter of and changes in the image of the subject's pupil on said image plane in response to light stimuli;
   an eye tracker for tracking movements of the subject's eye in response to moving light stimuli;
   data acquisition means responsive to said pupil diameter measuring means and said eye tracking means for generating dynamic measures of pupil diameter and movements of the subject's eye as a function of time;
   a database for storing baseline data for the subject; and
   a computer controlled by a stored program for controlling said light stimuli and receiving said dynamic measures of pupil diameter and movements, accessing said baseline data for the subject, and providing an output indicative of a deviation of said current measurements from said baseline data.

2. The fitness impairment tester as recited in claim 1 further comprising light stimulus means controlled by said computer for providing light stimuli on and off axis of said pupil imaging optics.

3. The fitness impairment tester as recited in claim 1 wherein a subject's personal identification number is stored with the subject's baseline data in the database, further comprising an identification input device for entering a subject's personal identification number, said computer correlating the entered personal identification with the personal identification number stored with the subject's baseline data.

4. The fitness impairment tester as recited in claim 1 wherein said pupil imaging optics comprises:

a source of infrared light;
optics forming an image of the source of infrared light and directing the infrared light toward the subject's pupil, said image being smaller than the smallest that the subject's pupil ever gets, infrared light passing through the subject's pupil and falling on the subject's retina where it is backscattered; and
an image sensor located at said image plane, the backscattered light exiting the subject's pupil being projected onto said image sensor.

5. The fitness impairment tester as recited in claim 4 wherein said image sensor is a video camera providing an output to said pupil diameter measurement means.

6. The fitness impairment tester as recited in claim 4 wherein said eye tracker comprises:
a tracking mirror rotatable about at least one axis, said tracking mirror directing the image of the source of infrared light to the subject's pupil and also directing the backscattered light exiting the subject's pupil onto said image sensor;
a beamsplitter intercepting the backscattered light exiting the subject's pupil and directing a portion of the backscattered light away from said image sensor; and
a detector positioned to receive said portion of the backscattered light directed away from said image sensor, said detector having at least two outputs connected to said computer to provide a measure of decentering of the backscattered light on said detector, said computer controlling the rotation of said tracking mirror to maintain the backscattered light from the subject's eye centered on the detector.

7. The fitness impairment tester recited in claim 6 further comprising blink detector means coupled to inhibit tracking by said eye tracker during a blink by the subject being tested.

8. The fitness impairment tester recited in claim 6 further comprising eye image acquisition means for automatically initiating a test of a subject upon acquiring an image of the subject's eye.

9. A method of testing fitness impairment of a subject comprising the steps of:
illuminating a subject's pupil and focusing an image of the subject's pupil on an image plane;
tracking movements of the subject's eye in response to moving light stimuli;
generating measures of one or more parameters $P_i$ of the subject's eye as a function of time;
storing baseline data for the subject in a database;
controlling light stimulus means and receiving said measures of said parameters $P_i$;
accessing said baseline data for the subject; and
providing an output indicative of a deviation of current measurements of said parameters $P_i$ from said baseline data.

10. The method of measuring fitness impairment of a subject as recited in claim 9 wherein the step of providing an output indicative of a deviation of said current measurements from said baseline data comprises the steps of:
computing a mean $\mu_i$ for each measured parameter $P_i$;
computing a standard deviation $a_i$ for each measured parameter $P_i$; and
computing an Index as $$\text{Index} = \sum_{i=1}^{n} \left( \frac{P_i - \mu_i}{\sigma_i} \right)^2,$$

where n is the number of parameters $P_i$, a large value of Index indicating that measured parameter values are very different than those of the baseline.

11. The method of measuring fitness impairment of a subject as recited in claim 10 wherein the parameter measured is Saccadic Velocity SV and the Index is computed as $$\text{Index} = \left( \frac{SV - \mu_{SV}}{\sigma_{SV}} \right)^2,$$

and the measurement of SV is a dynamic measurement.

12. The method of measuring fitness impairment of a subject as recited in claim 10 further comprising the step of measuring parameters of the image of the subject's pupil on said image plane in response to light stimuli and wherein the parameter measured is Latent LAT and the Index is computed as $$\text{Index} = \left( \frac{LAT - \mu_{LAT}}{\sigma_{LAT}} \right)^2,$$

and the measurement of LAT is a dynamic measurement.

13. The method of measuring fitness impairment of a subject as recited in claim 10 further comprising the step of measuring parameters of the image of the subject's pupil on said image plane in response to light stimuli and wherein the parameters are Saccadic Velocity SV and Latency LAT and the Index is computed as $$\text{Index} = \left( \frac{LAT - \mu_{LAT}}{\sigma_{LAT}} \right)^2 + \left( \frac{SV - \mu_{SV}}{\sigma_{SV}} \right)^2,$$

and the measurements of SV and LAT are dynamic measurements.

14. The method of measuring fitness impairment of a subject as recited in claim 13 wherein Amplitude AMP is measured and Index is computed as $$\text{Index} = \left( \frac{AMP - \mu_{AMP}}{\sigma_{AMP}} \right)^2 + \left( \frac{LAT - \mu_{LAT}}{\sigma_{LAT}} \right)^2 +$$

$$\left( \frac{SV - \mu_{SV}}{\sigma_{SV}} \right)^2,$$

and AMP is a dynamic measurement.

15. The method of measuring fitness impairment of a subject as recited in claim 14 wherein Initial Diameter INI is measured and Index is computed as $$\text{Index} = \left( \frac{INI - \mu_{INI}}{\sigma_{INI}} \right)^2 + \left( \frac{AMP - \mu_{AMP}}{\sigma_{AMP}} \right)^2 +$$

$$\left(\frac{LAT - \mu_{LAT}}{\sigma_{LAT}}\right)^2 + \left(\frac{SV - \mu_{SV}}{\sigma_{SV}}\right)^2.$$

16. The method of measuring fitness impairment of a subject as recited in claim 9 further comprising the step providing light stimuli on and off axis of said pupil imaging optics.

17. The method of measuring fitness impairment of a subject as recited in claim 9 wherein a subject's personal identification number is stored with the subject's baseline data in the database, said method further comprising the steps of:
  entering a subject's personal identification number prior to testing; and
  correlating the entered personal identification number with the personal identification number sorted with the subject's baseline data.

* * * * *